US00PP35366P2

(12) United States Plant Patent
Camposeo et al.

(10) Patent No.: US PP35,366 P2
(45) Date of Patent: Sep. 5, 2023

(54) OLIVE TREE NAMED 'OAC9805-01'

(50) Latin Name: *Olea europaea*
Varietal Denomination: 'OAC9805-01'

(71) Applicant: Agromillora Catalana S.A.U., Sant Sadurni d'Anoia (ES)

(72) Inventors: Salvatore Camposeo, Valenzano (IT); Gaetano Alessandro Vivaldi, Barletta (IT); Marisa Cunill, Barcelona (ES)

(73) Assignee: Agromillora Catalan S.A.

( * ) Notice: Subject to any disclaimer, the term of this patent is extended or adjusted under 35 U.S.C. 154(b) by 0 days.

(21) Appl. No.: 17/956,151

(22) Filed: Sep. 29, 2022

(51) Int. Cl.
*A01H 6/00* (2018.01)
*A01H 5/08* (2018.01)

(52) U.S. Cl.
USPC ..... Plt./158

(58) Field of Classification Search
USPC ..... Plt./158
CPC ..... A01H 6/00; A01H 5/08
See application file for complete search history.

*Primary Examiner* — Keith O. Robinson
(74) *Attorney, Agent, or Firm* — Cassandra Bright

(57) ABSTRACT

A new distinct cultivar of *Olea europaea* named 'OAC9805-01' is described, characterized by an upright to spreading habit, dark violet fruit color, and high fertility. Plants have a high frequency of mixed shoots that produce vegetative buds and flower buds. Resistance to leafspot (*Spilocaea oleagina*) has been observed. The new variety is an olive tree, suitable for high density olive orchards.

3 Drawing Sheets

Latin name of the genus and species: *Olea europaea.*
Variety denomination: 'OAC9805-01'.

BACKGROUND OF THE INVENTION

The present invention is a new and distinct variety of olive tree named 'OAC9805-01'. 'OAC9805-01' is the product of a planned breeding program by the inventor in Barcelona, Spain. The new cultivar is the result of a cross between the seed parent, *Olea europaea* 'Arbosana', unpatented, and the pollen parent, *Olea europaea* 'Koroneiki', unpatented.

'OAC9805-01' was selected as an interesting new variety in 2016. Asexual reproduction by way of rooting semi-ligneous stem cuttings was first performed during 2016, in Barcelona, Spain. Through 14 subsequent generations, the unique features of 'OAC9805-01' have proven to be stable and true to type.

SUMMARY OF THE INVENTION

The cultivar 'OAC9805-01' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'OAC9805-01' as a new and distinct *Olea europaea* cultivar:

1. Upright to spreading habit.
2. Dark violet fruit color.
3. High fertility.
4. High frequency of mixed shoots that produce vegetative buds and flower buds.
5. Suitability for high density orchard planting.
6. Resistance to leafspot (*Spilocaea oleagina*).

COMPARISONS TO PARENT VARIETIES

Plants of the new cultivar 'OAC9805-01' are similar to plants of the seed parent in most horticultural characteristics, however, plants of the new variety differ in the following:

1. The new variety produces darker violet fruit than the seed parent.

Plants of the new cultivar 'OAC9805-01' are similar to plants of the pollen parent in most horticultural characteristics, however, plants of the new variety differ in the following:

1. The new variety produces larger fruit than the pollen parent.
2. The new variety has exhibited resistance to leafspot, which the pollen parent has not.

COMMERCIAL COMPARISON

Plants of the new cultivar 'OAC9805-01' can be compared to *Olea* 'Lecciana', U.S. Plant Pat. No. 30,208. The varieties are similar in most horticultural characteristics, however, the new variety differs in the following:

1. The new variety produces violet colored fruit; this comparator produces gray fruit.

BRIEF DESCRIPTION OF THE PHOTOGRAPHS

The accompanying photographic illustration shows typical samples of fruit on 4-year-old specimens of the new variety, in color as nearly true as it is reasonably possible to make in a color illustration of this character. Plants were grown in Barcelona, Spain. Colors in the photograph may differ from the color values cited in the detailed botanical description below, which accurately describes the colors of the new variety.

DETAILED BOTANICAL DESCRIPTION

Figure 1:
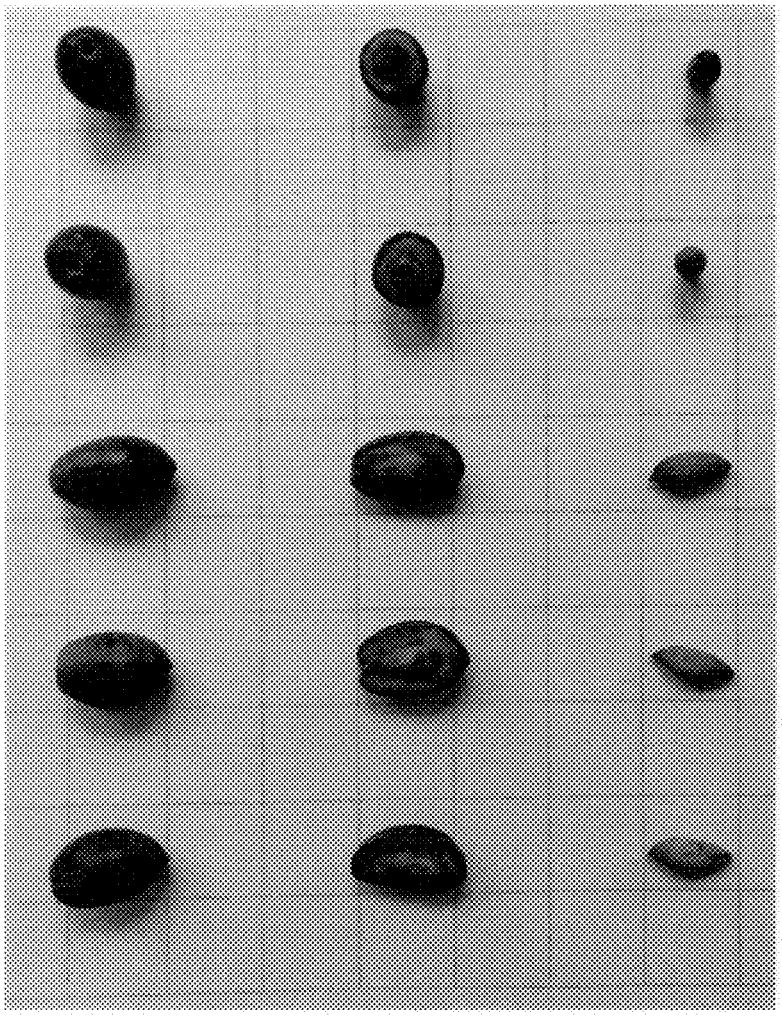
FIG. 1 illustrates ripe fruit, flesh and stones of 'OAC9805-01'.
Figure 2:
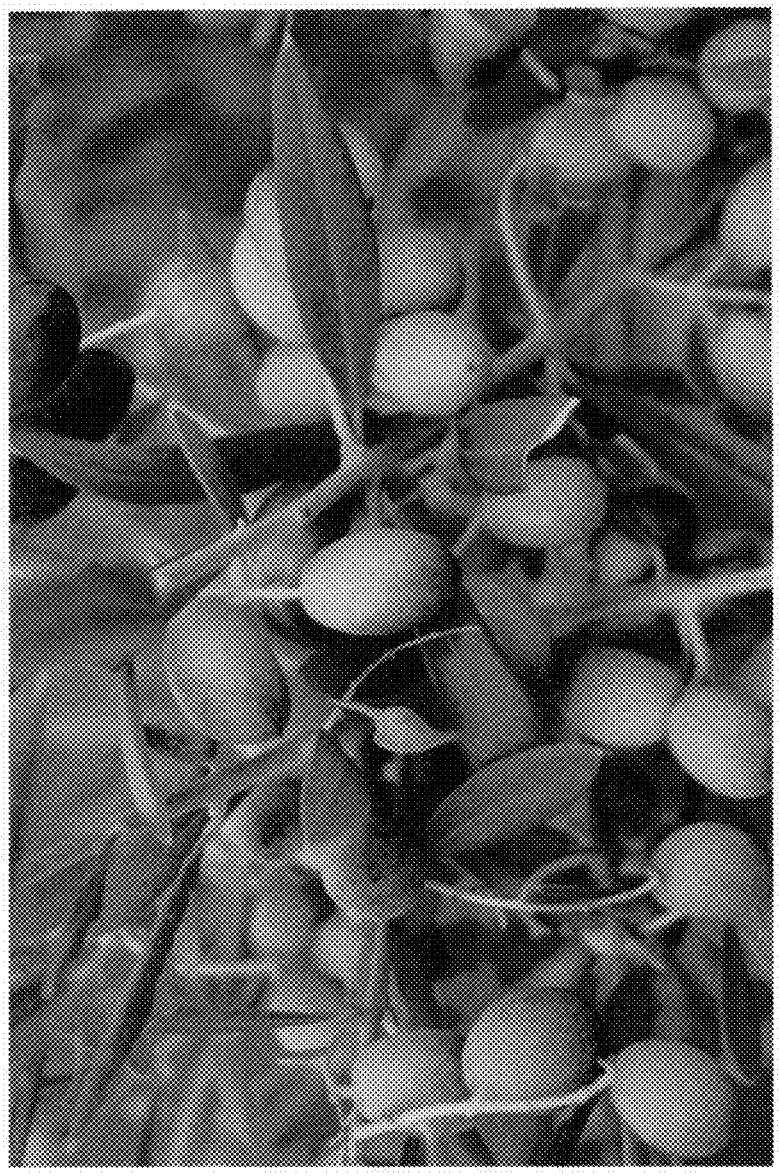
FIG. 2 illustrates ripening fruits of 'OAC9805-01'.
Figure 3:
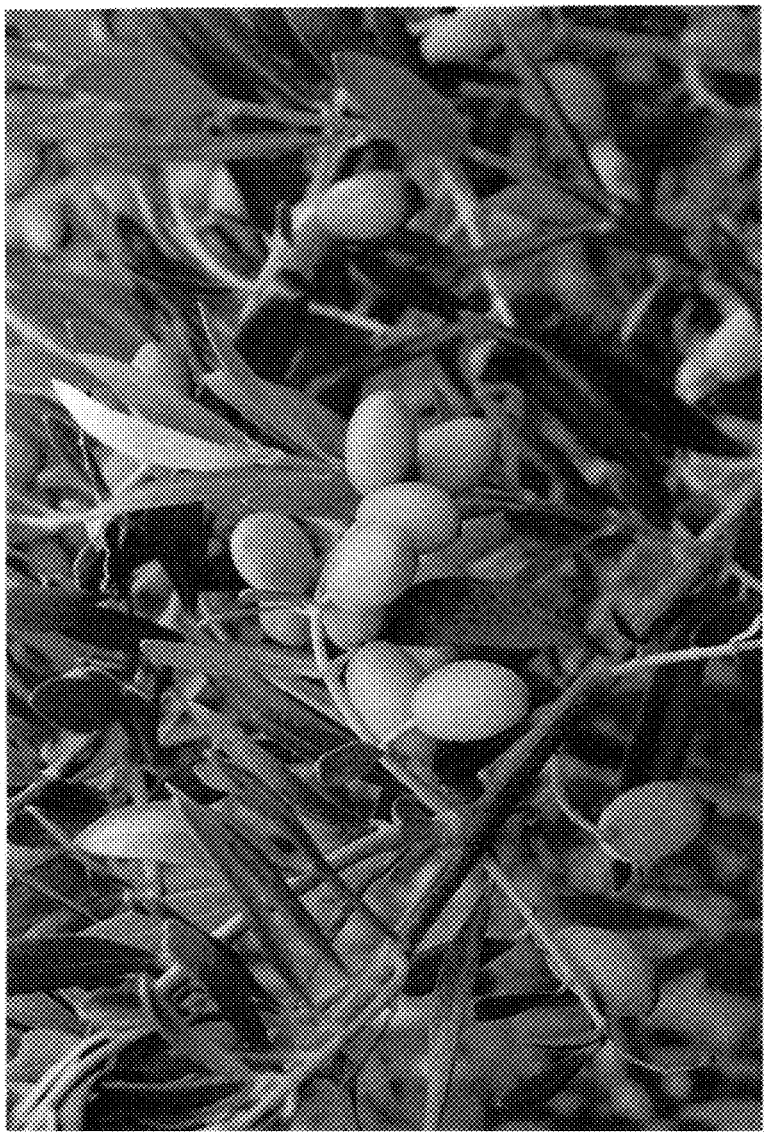
FIG. 3 illustrates unripe fruit of 'OAC9805-01'.

In the following description, color references are made to The Royal Horticultural Society Colour Chart 2007, except where general terms of ordinary dictionary significance are used. The following observations and measurements describe 'OAC9805-01' plants grown outdoors in Barcelona, Spain. The age of plant described is of 4 years, with an average height of 200 cm, a high canopy density, a 300 cm plant spread, a one-year growth rate to reach two meters high and 20 to 30 days to initiate roots at approx. 20° C. At observation location temperature ranged between 15° C. to 35° C. during the day, and between 5° C. to 20° C. during the night.

Botanical classification: *Olea europaea* 'OAC9805-01'.

PROPAGATION

Propagation method: Semi-ligneous stem cuttings.

PLANT

Age of the tree described: About 4 years.
Growth habit: Upright to spreading.
Plant vigor: Low.

FOLIAGE

Leaf:
- *Arrangement*.—Opposite.
- *Average length*.—4 to 6 cm.
- *Average width*.—About 1 cm.
- *Shape of blade*.—Elliptic.
- *Apex*.—Acute.
- *Base*.—Tapered.
- *Attachment*.—Petiolate.
- *Margin*.—Entire.
- *Texture of top surface*.—Glabrous.
- *Texture of underside*.—Very slightly pubescent.
- *Aspect*.—Flat with slight cupping under near margin.
- *Curvature of the longitudinal axis of leaf blade*.—Straight.
- *Color*.—Mature foliage upper side: Near Green 143A. Mature foliage under side: Near Green 138B.
- *Petiole*.—Length: About 3 to 5 mm. Width: About 2 mm. Pubescence: Glabrous. Color: Near Green 138C.

FLOWER

Inflorescence and flower type and habit: Panicle composed of perfect, simple cruciform, inconspicuous flowers.

Flower size:
- *Diameter*.—About 4 mm.
- *Depth*.—About 2 mm.

Petals:
- *Arrangement*.—Cruciform.
- *Petal quantity*.—4.
- *Length*.—About 3 mm.
- *Width*.—About 2 mm.
- *Texture*.—Glabrous.
- *Apex*.—Acute.
- *Base*.—Fused.
- *Margin*.—Entire.
- *Color*.—Near White 155A.

Calyx/sepals:
- *Quantity per flower*.—4.
- *Arrangement*.—Rotate.
- *Shape*.—Irregular orbicular.
- *Length*.—About 1 mm.
- *Width*.—About 1 mm.
- *Texture*.—Glabrous.
- *Color*.—Near Yellow-Green 145D.

REPRODUCTIVE ORGANS

Stamens:
- *Number*.—2.
- *Filament length*.—About 0.5 mm.

Anthers:
- *Shape*.—Hemispherical.
- *Length*.—1 mm.
- *Color*.—Near Yellow-Green 145C.
- *Pollen*.—Color: Near Yellow 4C.

Pistil:
- *Number*.—1.
- *Length*.—About 1 mm.
- *Style*.—Length: About 0.5 mm. Color: Near Yellow 4D.
- *Stigma*.—Shape: Conical, bifid. Color: Near Yellow 4C.

FRUIT

Weight: Average 1.52 grams.
Color: RHS Violet-Blue N92A.
Size: Average length 20 mm.
Symmetry: Weakly asymmetric.
Shape: Round.
Nipple: Moderate.
Stone shape: Very elongated. Symetric.
Stone length: Average about 12 mm.
Stone diameter: Average about 3 mm.
Stone weight: Low, about 0.5 gram.
Stone mucron: Present.
Stone rugosity: Medium.

OTHER CHARACTERISTICS

Disease/pest resistance: Resistance to *Spilocea oleagina* has been observed.

Temperature tolerance: Tolerant to USDA hardiness zones 8 through 10; exhibits good resistance to low temperatures.

What is claimed is:

1. A new and distinct cultivar of Olive tree named 'OAC9805-01' as herein illustrated and described.

* * * * *